United States Patent
Stetson (10) Patent No.: US 9,105,123 B2
(45) Date of Patent: Aug. 11, 2015

(54) NON-LINEAR PROJECTIONS OF 3-D MEDICAL IMAGING DATA

(71) Applicant: Carl Zeiss Meditec, Inc., Dublin, CA (US)

(72) Inventor: Paul F. Stetson, Piedmont, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 0 days.

(21) Appl. No.: 13/692,781

(22) Filed: Dec. 3, 2012

(65) Prior Publication Data

US 2013/0094720 A1 Apr. 18, 2013

Related U.S. Application Data

(63) Continuation of application No. 12/535,046, filed on Aug. 4, 2009, now Pat. No. 8,332,016.

(51) Int. Cl.
| | |
|---|---|
| A61B 6/00 | (2006.01) |
| G06T 11/00 | (2006.01) |
| G06T 15/08 | (2011.01) |
| A61B 3/14 | (2006.01) |
| A61B 3/10 | (2006.01) |

(52) U.S. Cl.
CPC .............. *G06T 11/003* (2013.01); *A61B 3/102* (2013.01); *A61B 3/14* (2013.01); *G06T 15/08* (2013.01)

(58) Field of Classification Search
USPC ............... 600/310, 356, 383, 400, 407, 437; 356/4.01, 4.07, 5.04, 479, 489, 494, 356/497, 515
See application file for complete search history.

(56) References Cited

U.S. PATENT DOCUMENTS

| | | | |
|---|---|---|---|
| 5,189,369 A | 2/1993 | Takane et al. | |
| 5,321,501 A | 6/1994 | Swanson et al. | |
| 5,459,570 A * | 10/1995 | Swanson et al. | 356/479 |
| 5,633,974 A | 5/1997 | Chia | |
| 5,779,641 A | 7/1998 | Hatfield et al. | |
| 6,436,049 B1 | 8/2002 | Kamiyama et al. | |
| 6,501,272 B1 | 12/2002 | Haacke et al. | |
| 6,505,064 B1 | 1/2003 | Liu et al. | |
| 6,609,793 B2 | 8/2003 | Norrby et al. | |
| 6,658,280 B1 | 12/2003 | Haacke | |
| 7,301,644 B2 * | 11/2007 | Knighton et al. | 356/479 |

(Continued)

FOREIGN PATENT DOCUMENTS

| | | |
|---|---|---|
| JP | 2009-6086 A | 1/2009 |
| JP | 2009-165710 A | 7/2009 |
| WO | 99/52072 A1 | 10/1999 |

OTHER PUBLICATIONS

Non Final Office Action received for U.S. Appl. No. 12/535,046, mailed on Dec. 12, 2011, 13 pages.

(Continued)

*Primary Examiner* — Unsu Jung
*Assistant Examiner* — Michael N Fisher
(74) *Attorney, Agent, or Firm* — Morrison & Foerster LLP (57) ABSTRACT

The present invention improves projection displays of volume data. Using the Minimum Intensity Projection (MinIP), fluid filled regions or other regions of hyporeflective tissue are displayed. By limiting the projection to partial volumes within the volume, differences in the scattering intensity within specific regions are isolated. In this way, hyperreflectivity of weakly scattering tissue can be assessed.

7 Claims, 4 Drawing Sheets

(56) References Cited

U.S. PATENT DOCUMENTS

| | | | |
|---|---|---|---|
| 7,365,858 | B2 | 4/2008 | Fang-Yen et al. |
| 7,884,945 | B2* | 2/2011 | Srinivasan et al. ............ 356/497 |
| 2004/0246440 | A1 | 12/2004 | Andino et al. |
| 2004/0263779 | A1 | 12/2004 | Schroder |
| 2006/0147098 | A1 | 7/2006 | Ghosh et al. |
| 2007/0291277 | A1 | 12/2007 | Everett et al. |
| 2008/0100612 | A1* | 5/2008 | Dastmalchi et al. .......... 345/418 |
| 2008/0204655 | A1* | 8/2008 | Kikawa et al. ................. 351/206 |
| 2008/0300485 | A1* | 12/2008 | Liu et al. ........................ 600/438 |
| 2008/0317318 | A1 | 12/2008 | Scheuering et al. |
| 2009/0003668 | A1 | 1/2009 | Matsumoto |
| 2009/0207378 | A1* | 8/2009 | Ito et al. ........................ 351/245 |

OTHER PUBLICATIONS

Final Office Action received for U.S. Appl. No. 12/535,046, mailed on Apr. 13, 2012, 14 pages.

Notice of Allowance received for U.S. Appl. No. 12/535,046, mailed on Aug. 9, 2012, 8 pages.

Bajraszewski et al., "Three-Dimensional in Vivo Imaging by Spectral OCT", Proc. of SPIE, vol. 5316, 2004, pp. 226-232.

Bhalla et al., "Diffuse Lung Disease: Assessment with Helical CT-Preliminary Observations of the Role of Maximum and Minimum Intensity Projection Images", Radiology, vol. 200, No. 2, pp. 341-347.

Boppart et al., "Noninvasive Assessment of the Developing *Xenopus* Cardiovascular System Using Optical Coherence Tomography", Proceedings of the National Academy of Sciences of the United States of America, vol. 94, Apr. 1997, pp. 4256-4261.

Boppart Stephen A., "Surgical Diagnostics, Guidance, and Intervention using Optical Coherence Tomography", Submitted to the Harvard-MIT Division of Health Sciences and Technology, Medical Engineering and Medical Physics Program in Partial Fulfillment of the Requirements for the Degree of Doctor of Philosophy in Medical and Electrical Engineering at the Massachu, May 1998, 237 pages.

Edelman et al., "Extracranial Carotid Arteries: Evaluation with "Blackblood" MR angiography", Radiology, vol. 177, No. 1, 1990, pp. 45-50.

Fingler et al., "Phase-Contrast OCT Imaging of Transverse Flows in the Mouse Retina and Choroid", Investigative Ophthalmology & Visual Science, vol. 49, No. 11, Nov. 2008, pp. 5055-5059.

Hausler et al., "Coherence Radar" and "Spectral Radar"—New Tools for Dermatological Diagnosis, Journal of Biomedical Optics, vol. 3, No. 1, 1998, pp. 21-31.

Leitgeb et al., "Performance of Fourier Domain vs. Time Domain Optical Coherence Tomography", Optics Express vol. 11, No. 8, Apr. 21, 2003, pp. 889-894.

Makita et al., "Quantitative Retinal-Blood Flow Measurement with Three-Dimensional Vessel Geometry Determination using Ultrahigh-Resolution Doppler Opticalcoherence Angiography", Optics Letters, vol. 33, No. 8, Apr. 15, 2008, pp. 836-838.

Napel et al., "STS-MIP: A New Reconstruction Technique for CT of the Chest", Journal of Computer Assisted Tomography, vol. 17, No. 5, 1993, pp. 832-838.

Narayana et al., "Three-Dimensional Helical Computed Tomography Cholangiography with Minimum Intensity Projection in Gallbladder Carcinoma Patients with Obstructive Jaundice: Comparison with Magnetic Resonance Cholangiography and Percutaneous Transhepatic Cholangiography", Journal of Gastroenterology and Hepatology, vol. 20, Issue 2, 2005, pp. 304-308.

Niemeijer et al., "Vessel Segmentation in 3D Spectral OCT Scans of the Retina", Proc. of SPIE, vol. 6914, 2008, pp. 69141R-1 through 69141R-8.

International Search Report received for PCT Patent Application No. PCT/EP2010/004694, mailed on Oct. 8, 2010, 8 pages.

Raman et al., "Curved-Slab Maximum Intensity Projection: Method and Evaluation", Radiology, vol. 229, No. 1, 2003, pp. 255-260.

Remy-Jardin et al., "Sliding thin Slab, Minimum Intensity Projection Technique in the Diagnosis of Emphysema: Histopathologic-CT Correlation", Radiology, vol. 200, No. 3, Sep. 1996, pp. 665-671.

Remy-Jardin et al., "Volume Rendering of the Tracheobronchial Tree: Clinical Evaluation of Bronchographic Images", Radiology, vol. 208, No. 3, Sep. 1998, pp. 761-770.

Rubin et al., "Volumetric Analysis of Volumetric Data: Achieving a Paradigm Shift.", Radiology, vol. 200, No. 2, 1996, pp. 312-317.

Salles et al., "CT of Pancreas: Minimum Intensity Projections", Abdominal Imaging, vol. 33, No. 2, 2008, pp. 207-213.

Tan et al., "MR Venography of Multiple Sclerosis", American Journal of Neuroradiology, vol. 21, No. 6, Jun.-Jul. 2000, pp. 1039-1042.

Wojtkowski et al., "Three-dimensional Retinal Imaging with High-Speed Ultrahigh-Resolution Optical Coherence Tomography", Ophthalmology, Oct. 2005, pp. 1734-1746.

Zawadzki et al., "Adaptation of a Support Vector Machine Algorithm for Segmentation and Visualization of Retinal Structures in Volumetric Optical Coherence Tomography Data Sets", Journal of Biomedical Optics, vol. 12, No. 4, Jul. / Aug. 2007, pp. 041206-1-041206-8.

Office Action received for Chinese Patent Application No. 201080034615.6, mailed on Dec. 9, 2013, 10 pages. (2 pages of English Translation and 8 pages of Official copy).

Office Action received for Japanese Patent Application No. 2012-523233, mailed on Feb. 12, 2014, 9 pages (5 page of English Translation and 4 pages of Official Copy).

Office Action Received for Japanese Patent Application No. 2012-523233, mailed on Feb. 3, 2015, 6 pages (3 pages of English Translation and 3 pages of Official Copy).

* cited by examiner

NON-LINEAR PROJECTIONS OF 3-D MEDICAL IMAGING DATA

PRIORITY CLAIM

The is a continuation of U.S. patent application Ser. No. 12/535,046, filed Aug. 4, 2009 the disclosure of which is incorporated herein by reference.

TECHNICAL FIELD

The present invention relates to non-linear projections of 3-D medical imaging data, and in particular to optical medical imaging such as Optical Coherence Tomography ("OCT") for use in diagnosis and monitoring of tissue health.

BACKGROUND

Volume imaging data has become prevalent in medical imaging modalities such as ultrasound imaging, magnetic resonance imaging, computed tomography, and Optical Coherence Tomography (OCT). Volume data has brought innovation to the medical field, making it possible to safely and noninvasively directly observe the internal structure of a body, in particular of a human body. In recent years, volume rendering image processing techniques have been used to reduce the volume data to images displayed for medical diagnosis. Volume rendering enables visualization of three-dimensional structures by displaying a 2D projection of the 3D structure on commercially available 2D display.

Optical Coherence Tomography (OCT) is a technology for performing high-resolution real time optical imaging in situ. OCT is an optical measurement and imaging technique using either low-coherent light from a broadband source or sweeping light from a tunable laser to create interference signals measuring backscatter intensity at depths along a sample path. This depth profile is commonly called an "A-scan". Laterally scanning the sample beam over a series of adjacent A-scans synthesizes cross-sectional images, creating a 2-D tomogram commonly called a B-scan. Typically, volumes are acquired by laterally scanning the sample beam over a series of B-scans; however alternative scan patterns, such as a spiral scan pattern, have been suggested to acquire volume data.

Evaluation of biological materials using OCT was first disclosed in the early 1990's (see U.S. Pat. No. 5,321,501, Swanson, et al.). More recently it has been demonstrated that frequency domain OCT (FD-OCT) has significant advantages in speed and signal to noise ratio compared to time domain OCT (Leitgeb, R. A., et al., (2003) *Optics Express* 11:889-894). In Spectral Domain OCT (SD-OCT), sometimes referred to as Frequency Domain OCT (FD-OCT) and sometimes also referred to as Spectral Radar (Hausler, G and Linder, M W, *Journal of Biomedical Optics* Vol. 3 No. 1 (1998) 21-31), the measurement is achieved by examining the spectral content of the interference pattern out of the interferometer.

Volume data is reduced from 3-D to 2-D for display on a monitor or when printed on paper. In U.S. Pat. No. 7,301,644, Knighton et al. disclosed a method for reducing 3-D data for 2-D display called en-face imaging. This technique takes the volume data (or an interesting volume subset of the 3-D dataset) and integrates the data along each A-line, creating a 2-D image from the 3-D dataset. This technique has proven to be a very useful tool for viewing the OCT volume data. In light of the above, there is a need in the art for additional methods for viewing 2-D images of 3-D volume OCT data. The present invention provides such additional methods for creating 2-D images from 3-D volume data sets to display medically relevant information.

SUMMARY

The present invention is defined by the claims and nothing in this section should be taken as a limitation on those claims. Advantageously, embodiments of the present invention provide additional means for obtaining and displaying medically relevant information extracted from volume data.

In accordance with one aspect of the present invention, a Minimum Intensity Projection (MinIP) is used to find a fluid filled region or region of retinal disruption within a volume of data.

In accordance with another aspect of the present invention, volume information has low-intensity speckle artifacts reduced prior to projection through a partial volume.

In accordance with yet another aspect of the present invention, the projection information is compensated for variations in illumination prior to display.

In accordance with yet another aspect of the present invention, the MinIP is found along a collection of A-lines and the coordinate locations of the minimal intensity points are stored. These locations are smoothed before the smoothed locations are displayed as a minimum intensity height map In accordance with yet another aspect of the present invention, the partial volume over which the MinIP is computed is determined at least partially as a function of at least one special location. The special location may be user defined, or automatically computed from the volume image data.

DETAILED DESCRIPTION

The embodiments expressed herein are examples and the descriptions presented have been chosen to illustrate the principles of the invention and its practical applications and not as a definition of the invention. Modifications and variations of the invention will be apparent to those skilled in the art. The scope of the invention is defined by the claims, which includes known equivalents and unforeseeable equivalents at the time of filing of this application.

Herein, an intensity projection of an image volume is a two dimensional intensity image derived from the image volume by casting projection rays through the volume and determining a single intensity to represent each ray. A maximum intensity projection (MIP) is created by first identifying the pixel in each ray that has the highest intensity. An image is then created by mapping the locations of the rays to locations in the image and setting the intensity of the pixel at each location to the highest intensity associated with that ray. Similarly, a minimum intensity projection (MinIP) is the intensity projection with the result chosen to be the minimum intensity along the ray. In general MIP and MinIP can be formed casting projection rays along the x-, y-, or z-axis, or in any direction whatsoever. In MIP, each selected point has the attribute that its intensity is greater than or equal to the intensity of any other point along the projection ray. Similarly, MinIP selects points according to the minimum attribute. Many other attributes may be ascribed to some point along the projection array. For example, the location nearest the upper surface of the volume through which the projection ray is cast with intensity equal to the median intensity along the projection ray provides another attribute by which a single image point may be selected for each projection ray. The maximum, minimum, and median are nonlinear functionals—they do not satisfy the additivity property of linear functionals. In contrast, summation and integration are linear functionals. For simplicity of exposition, MinIP will be the primary example used throughout this description and rays will normally be cast parallel to the z-axis.

In an imaging modality where a fluid filled region is less reflective than the surrounding tissue, the minimum intensity projection (MinIP) offers a unique display technique. The MinIP provides a 2-D projection of the boundary of the fluid filled region. In the early 1990s, minimum intensity projections were used in Nuclear Magnetic Resonance Imaging to find fluid filled regions (U.S. Pat. No. 5,189,369, Takane et al.). Ophthalmologic images present a unique challenge, since the eye itself is fluid filled and OCT images contain speckle, which is an interference pattern in the backscattered light that causes intensity variations in the image. Speckle can create a very low intensity reflection in the midst of highly reflective tissue. By the late 90's, systems for ray-casting projections through speckle reduced ultrasound volumes were disclosed (U.S. Pat. No. 5,779,641, Hatfield, et al.) Speckle can be reduced by spatial or frequency compounding, low pass filtering image data, or other means. These systems, however, fail to recognize the importance of casting the projection through a partial volume (i.e., through a limited volume region.)

In OCT, the preferred method for visualizing fluid has been to measure the overall macular thickness. This method may delineate pockets of fluid, but it does so imprecisely. The invention disclosed herein, using MinIP, is sensitive to extremely small pockets of fluid. In prior art efforts, automatic segmentation of fluid pockets was difficult to perform reliably, and manual intervention to correct errors in automatic segmentation is time consuming and operator dependent. While the embodiments enclosed herein do not provide volume information, they enable the visualization of fluid filled regions, which is most important for determining drug treatment. For laser treatment, knowing the lateral location and extent of fluid lesions is critical for precisely targeting treatment where it is needed.

The Minimum Intensity Projection (MinIP) is a projection algorithm that finds the minimum brightness along the projection path in a volume of data. MinIP solves the problem of viewing the volume image when looking for weak reflections or deep shadows. For imaging systems that image backscattered radiation, i.e., imaging systems like OCT, hyporeflective regions surrounded by more reflective regions are readily detectable. Not all anatomy of interest is strongly reflecting. Often anatomy of interest, such as hyporeflective pockets of fluid within the retina are weakly reflecting. Such anatomy may be best visualized using minimum intensity projections.

The Outer Nuclear Layer (ONL) is normally not as reflective as other retinal tissue. Tissue that backscatters more light than normal is hyperreflective. In converse, tissue that backscatters less light than normal is hyporeflective. Even in the presence of diseased or disrupted retina which may cause hyperreflectivity in the ONL, the ONL often remains less reflective than neighboring retinal tissue. Thus, even a hyperreflective ONL may be the least reflective tissue found along a projection line and thus the hyperreflective ONL will still appear in the MinIP, but it will be brighter than normal. Hyperreflectivity in the Outer Nuclear Layer and other normally dark regions of the retina also can appear over and around areas of retinal disruption.

As with most modern image processing procedures, the preferred MinIP implementation is by means of an electronic computational processing unit or CPU. The CPU might be a general purpose computer like a PC or workstation or a specialized CPU such as a digital signal processor (DSP), application specific integrated circuit (ASIC), field programmable gate array (FPGA) or any other integrated circuit, whether fully contained in a single package or distributed across multiple chips.

Figure 1:
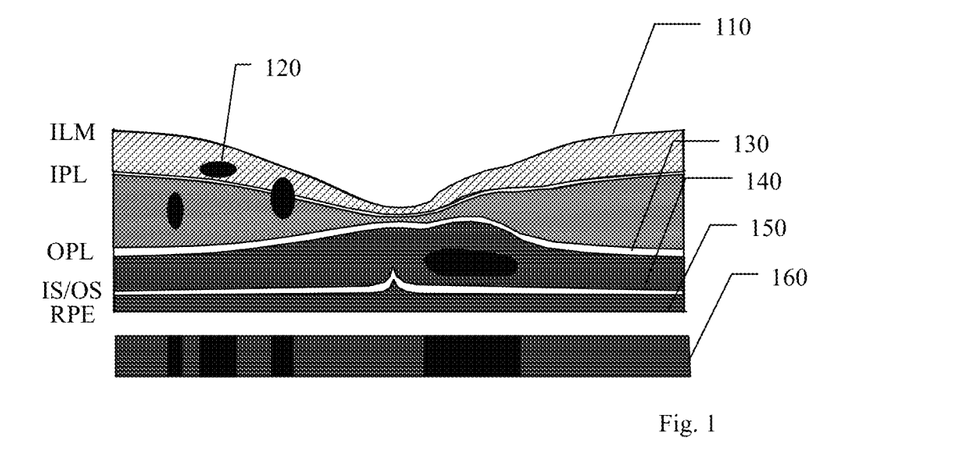
FIG. 1 is a schematic illustration of a MinIP display using the partial volume between the ILM and the RPE

In one embodiment of the invention, an OCT image volume and two segmented surfaces of the retina (e.g., ILM and RPE, or ILM and IS/OS) are required. The two segmented surfaces bound the partial volume through which the minimum projection is cast. The choice of surfaces may significantly impact the resulting MinIP display. The data depicted in FIG. 1 illustrates an example where the MinIP 160 is generated from the partial volume between the inner limiting membrane (ILM) 110 and the retinal pigment epithelium (RPE) 150. The illustrated strip 160 representing the MinIP has been widened for illustrative purposes. The projection cast along a ray is a single point or pixel. The wider band depicted here makes the MinIP intensity values easier to see.

For the example data depicted in FIG. 1, the MinIP 160 is the same whether it is generated from the partial volume between the ILM 110 and the RPE 160 or it is generated from the partial volume between the ILM and the boundary between the inner segment and outer segments of photoreceptors (IS/OS) 140. This is because the intensity depicted for the IS/OS is greater than the intensities depicted for neighboring tissue on either side of the IS/OS. Hence, the IS/OS intensity will not be the selected minimum. Furthermore, the depicted data has the intensity of the scattering tissue between the IS/OS and the RPE that is no less than the tissue above the IS/OS. Hence, the data from the IS/OS to the RPE in this example, do not change the intensity of the minimum intensity along the projection ray. This data was chosen for illustrative purposes and in no way implies that backscatter returned from below the IS/OS cannot have intensities less than the intensities derived from backscatter above the IS/OS. It can, but in this example, does not.

Figure 2:
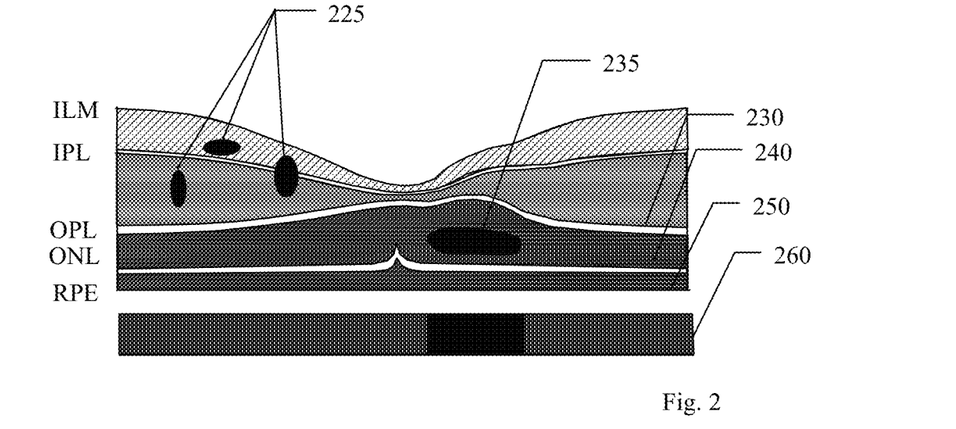
FIG. 2 is a schematic illustration of a MinIP display using the partial volume between the OPL and the RPE

FIG. 2 illustrates how the MinIP can change by changing the partial volume through which the projection ray is cast. FIG. 2 illustrates the same theoretical eye as FIG. 1. That is, the data illustrated in FIGS. 1 and 2 are the same. However, the MinIP 260 is generated from the partial volume between the outer plexiform layer (OPL) 230 and the RPE 250 whereas the MinIP 160 in FIG. 1 was generated from the partial volume between the ILM 110 and the RPE 150. The fluid filled region 235 is within the outer nuclear layer (ONL) 240. Because the MinIP in this example was cast between the OPL and the RPE, the fluid filled region 235 is readily apparent in the MinIP strip 260. However, the hyporeflective regions 225, which appeared in MinIP strip 160 are not visible in the MinIP strip 260 because they are not within the partial volume used to generate the display.

In an alternate embodiment of the invention, an OCT image volume and one segmentation of the retina (e.g., ILM, RPE, ILM, or IS/OS) is required. In this case, the segmented surface and a predefined or computed parameter or surface can define the partial volume through which the minimum projection is performed. The volume could be all points within a given distance of the surface; or it could be all points within a fixed depth below (or above) the surface, or all points within a range from a fixed offset to the surface, or other volume defined with respect to the surface. Alternatively, a surface can be defined by fitting a smooth surface to the segmented surface. The volume can be defined as the space between the surfaces or the space between a surface offset a fixed distance from the segmented surface to a surface offset a fixed distance from the computed surface, or other volume defined with respect to the two surfaces. In yet another embodiment of the invention, an image volume and an a priori defined subset of the volume are required. In this case, the partial volume through which the minimum projection is performed is chosen to be the a priori defined subset of the complete image volume.

Figure 3:
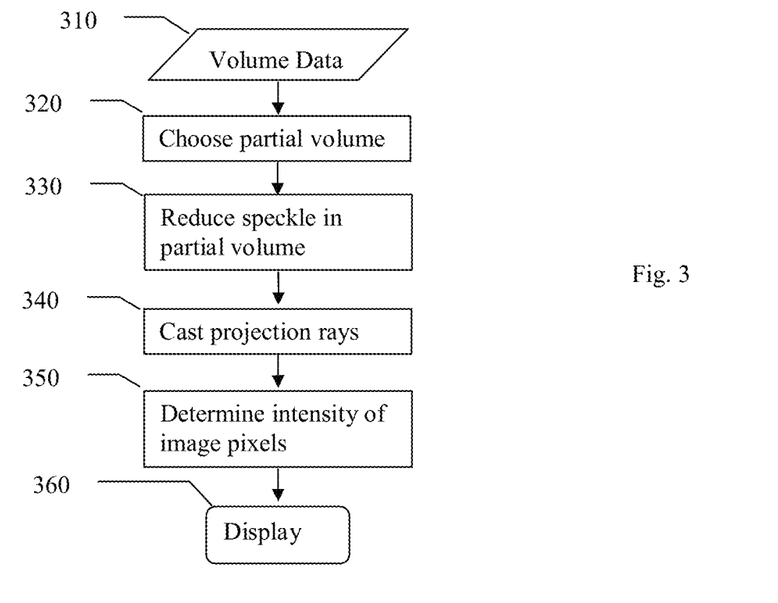
FIG. 3 is a flowchart of an embodied MinIP display application.

FIG. 3 is a flowchart of an embodied MinIP display application. A volume data 310 is input into the application. A partial volume is selected or chosen 320, either by one of the methods described above or by some other means for choosing a subvolume of the actual volume. The speckle is reduced in the partial volume 330, in one embodiment by a smoothing filter that is preferably larger than a speckle cell and smaller than the body to be imaged, or in other embodiments, by other image processing means. Rays are cast 340 through the partial volume and the location and intensity of the minimal intensity along each ray are determined 350. An image is formed from the minimal intensities and that image is displayed 360. The displayed image can be comprised of the minimum intensity values, or normalized minimum intensity values that are compensated for variations in illumination. The intensities within the ray are affected by what the light has passed through before entering the partial volume. Hence, when rays are cast in the direction of the illumination light (along the z-axis), a local compensation may be applied to the projection ray before computing the minimum, or, in particular if the compensation is linear, simply applied to the minimum selected from the ray. For example, the displayed values can be minimum intensity values normalized by the mean intensity along the projection ray within the partial volume. This normalization factor may be computed from points within the partial volume that are within a local neighborhood of the projection ray, or even points within the entire volume that are within a local neighborhood of the projection ray. Additionally, the display pixels can be smoothed to present a more appealing image. This is perhaps the simplest embodiment of the invention disclosed herein.

Minimum intensity projections determined according by the process of the preceding paragraph can have an "unnatural" look, in part because the depths from which the intensity displayed in the image is taken can be highly irregular, jumping greatly in depth even over small changes in X-Y. While determining the minimum intensity, we can save and then use the location within the image volume from which the minimum intensity was attained. We denote the depth at which the minimal intensity is attained by $z_{min}(x,y)$. That is, $z_{min}(x,y)$ is the depth of the location of the minimal intensity to be displayed at the (x,y) pixel of the MinIP image. We can improve the visual impression of the displayed image and get a more natural looking en-face image by fitting a smooth surface to the collection of points (x, y, $z_{min}(x,y)$) and then integrating the volume image intensities a certain margin above and below a smoothed surface. A two-dimensional quadratic or quartic surface generally gives a sufficiently smooth contour, although in some cases the fitting may not follow the desired anatomy because it is too smooth or the areas of abnormal anatomy were not properly excluded from the fitting. Technically, the en-face image generated by integrating in the neighborhood of a smoothly fit surface is no longer a minimal intensity projection display image. It does, however, require finding the minimal intensity projection voxels in order to compute the displayed image. In the limit where the en-face is only over a single pixel, the intensity values on the smooth surface are displayed.

Alternatively, the visual impression of the displayed image will appear more natural if the locations of the depths $z_{min}(x, y)$ are constrained to be within a local neighborhood. For example, the smoothed surface fitted to the collection of points (x, y, $z_{min}(x,y)$) can be used to define a new partial volume and the MinIP can be recomputed over this volume. Alternatively, it can be accomplished by first choosing a collection of MinIP points as good and recomputing the remaining points by constraining the search for the minimum intensity point at a neighboring location further within the partial volume so that neighboring MinIP is chosen from a set of points within a fixed distance of the location of the chosen neighbor.

In yet another alternative, an intensity other than the minimum intensity along the projection ray can be chosen. Grayscale image data intensities are distributed according to a Gaussian-like distribution in that the number of voxels with intensities near the mean is far greater than the number of voxels with intensities in the tails of the distribution. The minimum values of the image data along the rays in some regions will fluctuate statistically from ray to ray since the minima occur out in the sparsely populated tail of the intensity distribution. Selecting an intensity level slightly higher than the minimum, such as the 5th-percentile intensity, selects a portion of the intensity distribution that is more highly populated and thus less susceptible to statistical fluctuation, yet it preserves most of the characteristics of the minimum. Thus choosing the 5th percentile intensity value along the projection ray produces a smoother, less noisy image than the minimum intensity projection, although it may fail to depict fluid in locations where the total height of fluid-filled regions is less than 5% of the retinal thickness.

Figure 4:
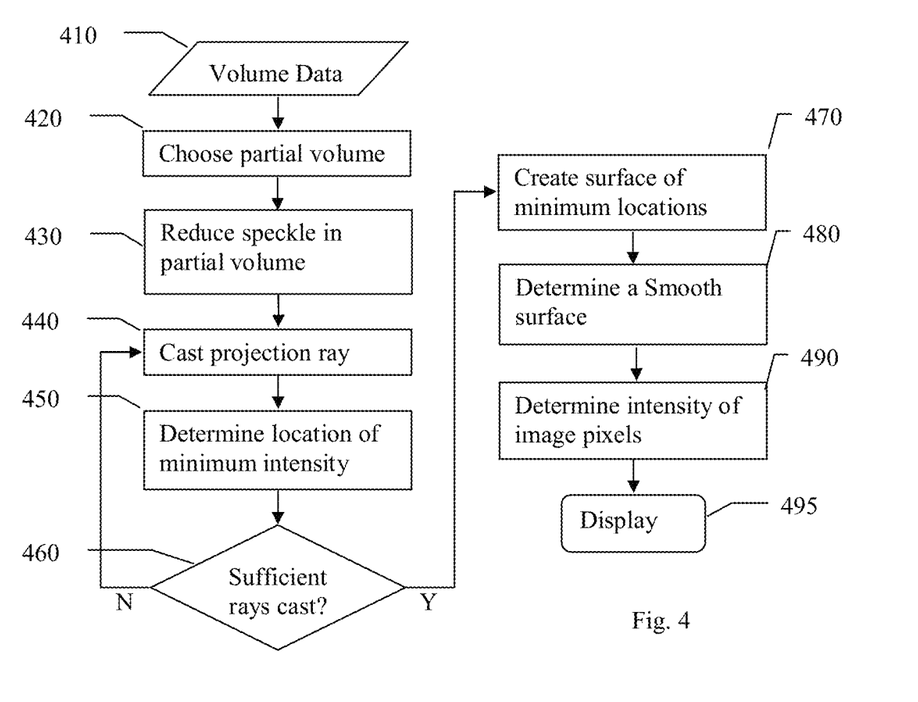
FIG. 4 is a flowchart of an embodied display application in which the location of the minimum intensity is used to determine a surface from which the displayed intensity is determined.

FIG. 4 depicts an alternative embodiment of the disclosed invention. The volume data is acquired 410 and a partial volume is selected 420. The speckle in the data is reduced 430 before rays are cast 440 and the location and intensity of the minimum intensity along the cast ray is determined 450. In this embodiment, the display intensities are indirectly determined from minimum values along the cast rays, so only those rays that are needed to implement the method are cast 460. In most cases, the more rays cast up to the resolution of the image volume, the better and more accurate the final display will be. The locations where the minimum intensities along the cast rays were found are points within the partial volume. A surface is determined from these locations 470. This surface may be the collection of location points themselves, or it may be a surface fit to those locations, or any surface otherwise determined from the location of the minimum intensity points. A smooth surface is determined 480 either directly from the points so that the smoothed surface of 480 is the same as the surface of 470, or the smooth surface is determined from the surface of 470. This smooth surface should be within the volume. The intensity of image pixels within the volume are used to determine intensities at locations on the smooth surface 490 and the intensities on the smooth are used to create an image for display 495. As in the previous example, the displayed image can be comprised of the computed intensity values, or normalized computed intensity values that are compensated for variations in illumination. Additionally, the display pixels can be smoothed to present a more appealing image.

Alternatively, the locations of the minimum intensity pixels can be used to create a minimum intensity height map. That is, a map of the height of the minimum intensity locations can be determined. When the projection ray is cast parallel to the Z-axis, the height is just the location along the ray (or a constant offset from that location, depending on the origin from which the height is calculated). If the projection ray is not parallel to the Z-axis, but is rather at an angle θ to the Z-axis, then the actual height is proportional to the location of the minimal intensity along the ray for the appropriate choice of origin. The proportionality is constant for all rays. The minimum intensity height map can be displayed as a surface rendered from a 3-D volume or as a 2-D image, with the height encoded by color or brightness. This height may be usefully displayed relative to the location of the RPE or some other segmented or fitted surface from the image volume.

In light of FIG. 4, instead of the locations of minimum intensity along the projection ray depicted in 470, we can choose the location along the projection ray where the intensity attains, for example, the $5^{th}$ percentile value. We can take the locations where these values were attained and use them (instead of the minimum locations) to determine the surface of 470. Of course, statistically as we move closer to the 50th percentile, the likelihood of finding more than one location with the same intensity increases. In this case, when implementing methods following the style of FIG. 4, a choice must be made, choosing one of the locations. This choice can simply be the first such point found, with the obvious bias attached, or we can choose locations based on the nearness of local clustering. Other means of choosing one location from the collection of locations will be obvious to those versed in the art.

Many forms of acquired image data contain an image artifact called speckle. Image speckle is a phenomenon generally associated with wave imaging and occurs as a result of wave interference at the detector. OCT and ultrasound image data (either 2-D or volume) generally contain speckle. The interference of various waveforms causes fluctuations of the detected intensity within the image volume. Volume image data with speckle should have at least a mild speckle reduction process performed to reduce the null intensities created in the neighborhood of high intensity reflections before performing a minimum intensity projection. Mild speckle reduction is preferred because it is generally sufficient to remove deep nulls in the neighborhood of strong reflections and stronger speckle reduction techniques generally require more data, take longer, and/or smear the data. Generally averaging across twice the speckle diameter is sufficient. After speckle reduction, each axial scan is analyzed for the minimum intensity, i.e., the darkest gray level, between the segmentation boundaries or through the partial volume.

Alternatively, a projection through the partial volume in a direction different from the axial scan direction can be performed. This generally requires interpolation and incurs inefficiencies in computational speed. Hence, projection along the axial direction is preferred.

As discussed previously, one approach to removing the "unnatural" look of the MinIP display is to integrate an en-face about a smooth surface derived from the collection of locations where the minimum intensities were attained. Another alternative for removing this "unnatural" look of the display is to globally define the minimum. That is, we can define a metric over a collection of intensity projections and choose the intensity projection of minimal intensity to display.

For example, if $z_{ILM}(x,y)$ represents the ILM segmentation and $z_{RPE}(x,y)$ represents the RPE segmentation, then a family of surfaces between the ILM and RPE is represented by:

$$z_{mix}(f, x, y) = f^* z_{ILM}(x, y) + (1-f)^* z_{RPE}(x, y)$$

where f is a desired fraction between 0 and 1, chosen to produce a dark image generally falling in the ONL. For example, a set of images for f=0.1, 0.2, . . . , 0.9 can be generated and the image with the minimum median intensity can be selected.

Any family of surface projections of the volume can be chosen whereby a metric can be applied by which a minimum surface can be chosen. The metric can be the median intensity of a projection or the average intensity of a surface or the absolute minimum intensity of a surface or any other metric. The metrics of the family of projections are compared and that projection with the minimum metric is chosen for display. If more than one surface has the same minimal value as its metric, a system for choosing one of these must be chosen. We can choose the first one with the minimum value or the last one with the minimum value. Alternatively, the choices can be displayed and one can be chosen by an operator. Alternatively, when the family is parameterized, the surface with parameter closest to a fixed value may be chosen.

Whether we smooth the collection of locations where the minimal intensity is found and integrate an en-face about that smoothed surface, or we fit a smooth surface to the collection of locations where the minimal intensity is found and integrate an en-face about that smooth surface, or we choose a collection of smooth surfaces and find the minimum amongst them, the projection provides an image that is like a MinIP but has less discontinuity from changing depths of the displayed data. They will be different from the MinIP, though, in that they may not depict small pockets of fluid or other small dark areas because of the constraints on the smoothness of the imaged surface.

The Outer Nuclear Layer (ONL) 240 has had little attention paid to it in OCT research, in part because it is difficult to segment. The minimum intensity in the healthy macula usually lies within this layer. The ONL is significantly more reflective where retinal disruptions occur, e.g., in the vicinity of retinal fluid pockets or over sub-RPE fluid. Longitudinal clinical studies may show whether this hyperreflectivity predicts future locations of pathology. The axial location of the minimum intensity relative to the RPE may also indicate focal disruptions in the retina, with increased height indicating hyperreflectivity in the outer retina.

Some of the interesting information in Minimum Intensity Projections (MinIPs) comes from looking at the hyperreflectivity of the ONL that can be caused by disruption of the retina. For this type of imaging, the partial volume through which the minimum intensity is projected must contain the ONL. The minimum intensity lies in the ONL about 99% of the time in healthy areas of the retina. If we do not have a good reliable ONL segmentation, MinIPs are an alternative way to examine the hyperreflectivity of the ONL (although bright regions in a MinIP can also mean the ONL has atrophied away completely). To ensure that you are looking at the ONL, it is best to limit the partial volume to the region between the OPL surface and the IS/OS surface. Since the IS/OS may sometimes be absent or invisible in the OCT images, limiting the partial volume between the OPL and RPE is more reliable. Even the OPL is difficult to segment and the results remain interesting when the partial volume is taken between the ILM and the RPE. Alternatively, the partial volume can be taken to be a volume above the RPE to a fixed distance above the RPE or the volume above the RPE to a surface that is a percentage of the distance from the RPE to the ILM. These partial volumes can generally be used to incorporate a large portion if not all of the ONL. Though the partial volume may contain other tissue, the surrounding tissue is generally brighter and thus will only appear in the MinIP when the ONL is severely disrupted and is even more hyperreflective than the MinIP indicates at that point.

Figure 5:
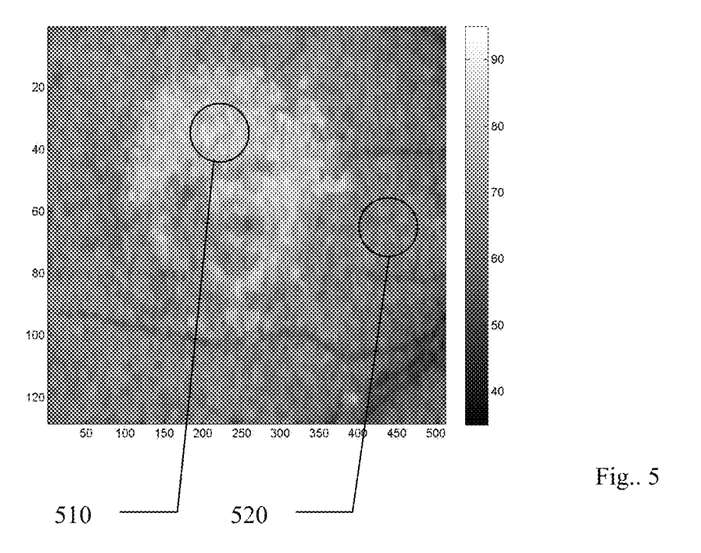
FIG. 5 is an image showing hyperreflective tissue.

FIG. 5 is a MinIP image using a partial volume taken between the ILM and the RPE and containing hyperreflective tissue in the ONL. An area of hyperreflectivity is found within the circle 510. This region is determined to be hyperreflective because the average intensity within the region 510 is significantly higher than the average intensity of a normal region 520. Hyperreflectivity can be determined using statistics other than the mean, such as the median. Any statistic which provides a statistically meaningful distinction between normally reflective tissue and abnormally reflective tissue will suffice, though the quality of the results may vary.

Figure 6:
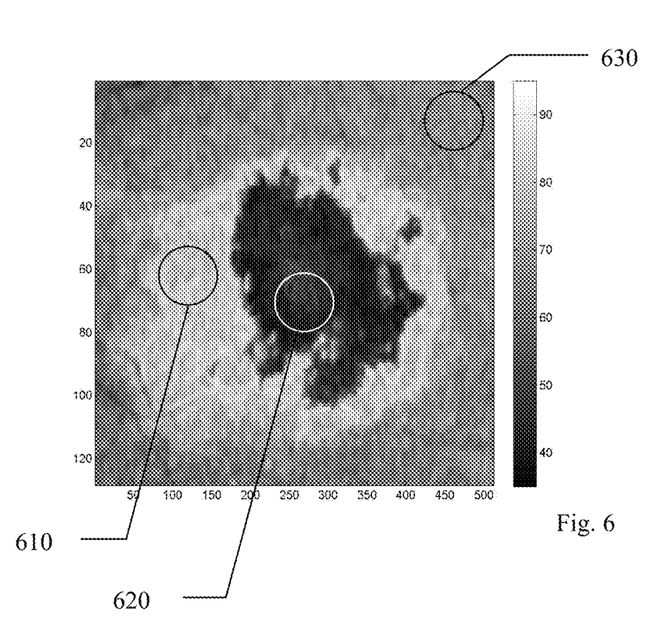
FIG. 6 is an image showing both hyperreflective and hyporeflective tissue.

FIG. 6 is another MinIP image, again using a partial volume taken between the ILM and the RPE and containing hyperreflective and hyporeflective tissue in the ONL. An area of hyperreflectivity is found within the circle 610. This region is determined to be hyperreflective because the average intensity within the region 610 is significantly higher than the average intensity of a normal region 630. An area of hyporeflectivity is found within the circle 620. This region is determined to be hyporeflective because the average intensity within the region 620 is significantly lower than the average intensity of a normal region 630. Any statistic which provides a statistically meaningful distinction between normally reflective tissue and abnormally reflective tissue will suffice, though the quality of the results may vary.

Figure 7:
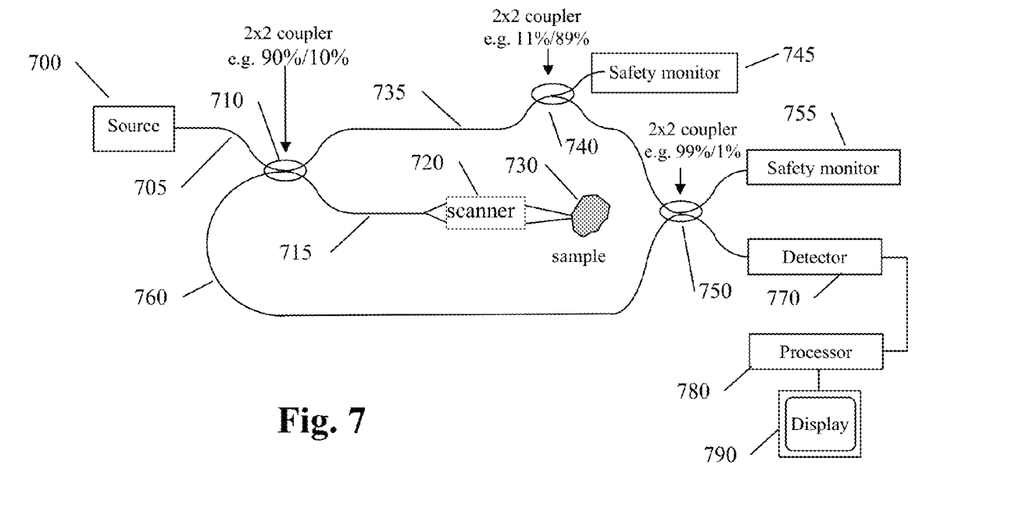
FIG. 7 illustrates one design of an optical coherence tomography system.

FIG. 7 illustrates an OCT device which can be used to implement the subject invention. Further information about this type of OCT device is disclosed in U.S. Patent Publication No. 2007/0291277, incorporated herein by reference. A low coherence light source 700, typically a superluminescent diode (SLD), is coupled to source fiber 705 that routes light to directional coupler 710. The optimal directional strength of the coupling depends on system design choices and may be 90/10 (as shown in FIG. 7) or 70/30 or other choices depending on SLD back reflection tolerance, the source illumination required to image the sample and other system design parameters. Directional coupler 710 splits the light into sample fiber 715 and reference fiber 735. The sample path may include a delay apparatus (not shown) to adjust the length of the sample path. The transverse scanner 720 deflects the OCT beam and preferably creates a focus in the beam near the region of interest in sample 730. The transverse scanner laterally scans the optical beam across the sample in order to image a volume of the sample.

Some light scattered from sample 730 returns through the scanner and delay apparatus to sample fiber 715. Coupler 710 routes this light through loop 760 to fiber coupler 750, where it interferes with the reference light. The combining coupler 750 provides two outputs. These outputs can be used for balanced detection (see U.S. Pat. No. 5,321,501, FIG. 10). Alternatively, the coupling ratio of coupler 750 can be adjusted to send most of the interfered light to a single OCT detector 770. Each OCT detector can be a single photodetector for use in time-domain OCT or swept-source OCT, or a spectrometer for use in spectral domain OCT.

Optional tap 740 diverts a fraction of the reference light to detector 745, which may be used to monitor the source power. Monitoring may be included to monitor the safety of the sample or to detect a degradation in the source 700. Alternatively, monitoring may not be included at all in the system. The tap removes some fraction of optical power from the reference fiber 735, reducing the power that reaches coupler 750. Sensitivity in OCT can reach the shot-noise limit if the reference power is large enough to bring the interference signal above receiver noise, but not so large as to bring intensity noise or beat noise above the level of shot noise.

The coupling ratios in directional couplers 710, 740 and 750 are chosen to set a safe level of illumination to the sample, and to set the appropriate reference power at the detector or detectors. For example, in the case of ophthalmic OCT of the retina using light with wavelengths near 850 nm, the safe exposure level is approximately 0.5 mW, and the optimum reference level at the detector is approximately 0.005 mW. Sources are available in this wavelength range having output power of approximately 5 mW. For these conditions one would use a coupling ratio near 90%/10% in the splitting coupler 710 so that 10% of the source power reaches the sample. 90% of the backscattered light will then be routed to loop 760. In the case where there is a single OCT detector 770, the combining coupler 750 preferably routes most of the sample light to that detector. The splitting coupler 710 routes 90% of source light, 4.5 mW, to reference fiber 735, while only 0.005 mW is required at the detector. One could use a combining coupler 750 that couples 0.1% of the reference light into the single OCT detector 770, but in manufacture it is difficult to control the 0.1% coupling factor. A preferred solution is to use a 99%/1% split ratio in combining coupler 750, and take advantage of the additional degree of freedom in tap 740 to adjust the reference power. Nominally, tapping 89% of the power form reference fiber 735 will provide an appropriate reference level of 0.005 mW at OCT detector 770, in this example.

As an alternative to adjusting the tap ratio of optional tap 740, one can adjust the reference level by including attenuating fiber (U.S. Pat. No. 5,633,974) in the reference path.

The output of the detector 770 is routed to processor 780. This processor may be a single device or a plurality of devices, preferentially optimized for their portion of processing. The processor 780 is connected to one or more peripherals providing a user interface devices, such as display 790. The processor might also be connected to other user interface devices (such as a keyboard, mouse, joystick, and others), and one or more external communication devices (such as a USB or network connector, optical storage media, printer, internet, and others), as well as possibly connecting to other imaging hardware (such as cameras, fixation targets, fundus viewers, and others) or peripheral patient devices (such as head support, height adjustment, and others) which are not shown. The processor 780 provides the computational power (in one or more modules) processing functions such as image formation, volume rendering, segmentation, registration, evaluation of cost functions, and/or other computational tasks required for medical imaging and analysis. Processed results may be displayed on display 790 or stored locally on a local storage device (not shown) or stored or displayed externally using one or more of the processor's external communication devices.

It should be understood that the embodiments, examples and descriptions have been chosen and described in order to illustrate the principles of the invention and its practical applications and is not intended to be exhaustive or to limit the invention to the precise form disclosed. Modifications and variations of the invention will be apparent to those skilled in the art in light of the above teaching. For example, while extrema are described herein as minimums, under an alternative metric, the invention can be performed using maximums. The embodiments were chosen and described to explain the principles of the invention and its practical application to enable others skilled in the art to best use the invention in various embodiments and with various modifications suited to the particular use contemplated. The scope of the invention is defined by the claims, which include known equivalents and unforeseeable equivalents at the time of filing of this application.

The following references are hereby incorporated herein by reference.

U.S. PATENT DOCUMENTS

U.S. Pat. No. 5,189,369 Takane et al., NMR imaging method of low flow rate fluid
U.S. Pat. No. 5,321,501 Swanson, et al., Method and apparatus for optical imaging with means for controlling the longitudinal range of the sample
U.S. Pat. No. 5,779,641 Hatfield, et al., Method and apparatus for three-dimensional ultrasound imaging by projecting filtered pixel data
U.S. Pat. No. 6,436,049 Kamiyama et al., Three-dimensional ultrasound diagnosis based on contrast echo technique
U.S. Pat. No. 6,501,272 Haacke, et al. Application-specific optimization of echo time in MR pulse sequences for investigating materials with susceptibilities different from that of the background in which they are embedded
U.S. Pat. No. 6,505,064 Liu et al., Diagnostic imaging systems and methods employing temporally resolved intensity tracing
U.S. Pat. No. 6,658,280 Haacke; E. Mark, Susceptibility weighted imaging
U.S. Pat. No. 7,301,644 by Knighton et al., Enhanced optical coherence tomography for anatomical mapping
2008/0100612 Dastmalchi; Shahram Shawn et al., User interface for efficiently displaying relevant OCT imaging data
2007/0291277 Everett; Matthew J.; et al., Spectral domain optical coherence tomography system

OTHER PUBLICATIONS

Leitgeb, R. A., et al. (2003). "Performance of Fourier domain vs. time domain optical coherence tomography." *Optics Express* 11(8): 889-894.
Häusler, G. and M. W. Lindner (1998). ""Coherence Radar" and "Spectral Radar"—New Tools for Dermatological Diagnosis." Journal of Biomedical Optics 3(1): 21-31.
Napel S, Rubin G D, Jeffrey R B Jr., "STS-MIP: a new reconstruction technique for CT of the chest", J. Comput Assist Tomogr 1993; 17:832-838.
Narayana D L V Rao, Manpreet Singh Gulati, Shashi Bala Paul, Girish Kumar Pande, Peush Sahni and Tushar Kanti Chattopadhyay, "Three-dimensional helical computed tomography cholangiography with minimum intensity projection in gallbladder carcinoma patients with obstructive jaundice: Comparison with magnetic resonance cholangiography and percutaneous transhepatic cholangiography", Journal of Gastroenterology and Hepatology, Volume 20, Issue 2, Pages 304-308, 19 Jan. 2005.
A. Salles, M. Nino-Murcia, R. Jeffrey, "CT of pancreas: minimum intensity projections", Abdominal Imaging, Volume 33, Number 2, March 2008, pp. 207-213(7).

What is claimed is:

1. A method of analyzing optical coherence tomography (OCT) image data of an eye, said eye being examined by an OCT system, said OCT system including a light source for generating a beam of light, a sample arm, a reference arm, and a detector for measuring light combined from the sample and reference arms said method comprising:
   a. scanning the beam of light over a region of the eye via the sample arm;
   b. combining the light from the sample and reference arms;
   c. measuring the combined light;
   d. generating three dimensional volume image data corresponding to structures within the eye from the combined light;
   e. identifying two anatomical surfaces within the image data, wherein each anatomical surface is described by a set of physical coordinates;
   f. determining a mathematically defined, non-anatomical additional surface located between the two identified anatomical surfaces, wherein the coordinates of the additional mathematically defined surface are represented as a mathematical combination of the coordinates of the two identified anatomical surfaces; and
   g. storing the coordinates of the additional mathematically defined surface for further analysis or displaying an image of the eye using the identified additional mathematically defined surface.

2. A method as recited in claim 1, wherein the mathematical relationship between the two identified surfaces is:

$$Z_{addsurf}(x,y) = f^* Z_{surf1}(x,y) + (1-f)^* z_{surf2}(x,y),$$

wherein f is a desired fraction between 0 and 1.

3. A method as recited in claim 1, wherein the two identified surfaces are the retinal pigment epithelium (RPE) and the inner limiting membrane (ILM).

4. A method as recited in claim 2, wherein a family of additional surfaces is determined.

5. A method as recited in claim 4, wherein the family of additional surfaces is used to define subvolumes of image data, said subvolumes having less than all the generated image data, said subvolumes being bounded by the family of surfaces.

6. A method as recited in claim 5, further comprising identifying a subvolume from the collection of subvolumes using a metric to characterize an intensity attribute of the subvolume.

7. A method as recited in claim 3, wherein the additional surface is a percentage of the distance from the RPE to the ILM.

* * * * *